United States Patent [19]

Rieck, III et al.

[11] Patent Number: 5,030,725
[45] Date of Patent: Jul. 9, 1991

[54] METHOD OF RESOLVING CIS 3-AMINO-4-[2-(2-FURYL)ETH-1-YL]-1-METHOXYCARBONYLMETHYL-AZETIDIN-2-ONE USING (−)-DAG

[75] Inventors: John A. Rieck, III, Indianapolis; Ian G. Wright, Greenwood, both of Ind.

[73] Assignee: Eli Lilly and Company, Indianapolis, Ind.

[21] Appl. No.: 475,515

[22] Filed: Feb. 6, 1990

[51] Int. Cl.$^5$ .................. C07B 57/00; C07D 205/085
[52] U.S. Cl. ..................................... 540/364; 548/433
[58] Field of Search ......................................... 540/364

[56] References Cited

U.S. PATENT DOCUMENTS

| | | | |
|---|---|---|---|
| 3,904,632 | 9/1975 | Hollander | 546/74 |
| 4,167,581 | 9/1979 | Smith | 514/522 |
| 4,711,887 | 12/1987 | Briggs | 544/239 |
| 4,923,983 | 4/1990 | Wright | 540/364 |
| 4,931,556 | 6/1990 | Boyer et al. | 540/364 |
| 4,931,557 | 6/1990 | Brennan et al. | 540/364 |

OTHER PUBLICATIONS

Mohacsi, I Organic Syn 55, 80–84 (1976).
Mohacsi II, Organic Syn 53, 1881 (1973).
Fitzi, Tetrahedron 44, 5277 (1988).
Brossl, J. Org. Chem 35, 3559 (1970).

*Primary Examiner*—Mark L. Berch
*Attorney, Agent, or Firm*—William C. Martens; Leroy Whitaker

[57] ABSTRACT

Cis α,α/β, β-3-amino-4-[2-(2-furyl)eth-1-yl]-1-methoxycarbonylmethyl-azetidin-2-one is resolved via (−)-2,3:4,6-di-O-isopropylidene-2-keto-L-gulonic acid hydrate (DAG).

1 Claim, No Drawings

METHOD OF RESOLVING CIS 3-AMINO-4-[2-(2-FURYL)ETH-1-YL]-1-METHOXYCARBONYLMETHYL-AZETIDIN-2-ONE USING (−)-DAG

BACKGROUND OF THE INVENTION

An important clinical trial candidate, (6R,7S) 7-(R)-phenylglycylinamido-3-chloro-1-azabicyclo[4.2.0]-oct-2-en-8-on-2-carbonxylic acid (loracarbef) may be synthesized by various routes. One of the more noteworthy total syntheses of loracarbef is that made possible by Evans and Sjogren, U.S. Pat. No. 4,665,171. The Evans and Sjogren methodology provides a chiral 2+2 (ketene plus imine) cycloaddition, and accordingly, entry to a wide variety of chiral cis β-lactams. However, the Evans and Sjogren methodology provides for the utilization of a chiral auxiliary of the formula

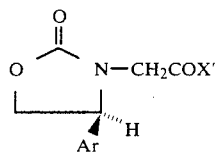

in the 2+2 cycloaddition with a Schiff's base, wherein X' is chloro, bromo, trifluoroacetoxy, or —OP(=)X$_2$, wherein X is halogen. The above chiral auxiliary is synthesized in seven steps from L-phenylglycine. The resulting cycloaddition provides compounds of the formula

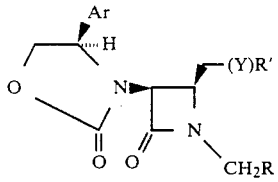

wherein Ar is phenyl, C$_1$-C$_4$ alkylphenyl, halophenyl, C$_1$-C$_4$ alkoxyphenyl, naphthyl, thienyl, furyl, benzothienyl, or benzofuryl; R is phenyl, C$_1$-C$_4$ alkylphenyl, C$_1$-C$_4$ alkoxyphenyl, or halophenyl; Y is —CH=CH—, or —CH$_2$-CH$_2$—; and R' is phenyl, C$_1$-C$_4$ alkylphenyl, C$_1$-C$_4$ alkoxyphenyl, halophenyl, furyl or naphthyl.

The obvious shortcomings of the Evans and Sjogren route are that a very expensive starting material, L-phenylglycine, is used, the chiral auxiliary is synthesized in several steps in linear fashion; and further, the chiral auxiliary is removed and discarded using Li/NH$_3$/t-C$_4$H$_9$ OH to provide a free 3-aminoazetidinone.

As an achiral alternative, Hatanaka et al., Tetrahedron Letters Vol. 24, No. 49, pp 4837-4838 (1983), provides a method of preparing a 3-hydroxy(±)-1-carbacephalosporin via a 2+2 cycloaddition much in the same fashion as that of Evans and Sjogren, but without the use of a chiral auxiliary as the ketene source. The Hatanaka methodology provides many of the same intermediates as does the Evans and Sjogren synthesis, albeit in achiral form. The advantage of the achiral synthesis is economy of steps and starting material. However, a resolution step is necessary to obtain the desired β, β isomer free from the α, α isomer.

SUMMARY

Cis 3-amino-4-[2-(2-furyl)eth-1-yl]-1-methoxy-carbonylmethyl-azetidin-2-one is resolved by the practice of this invention into its enantiomeric cis α, α and cis β, β components whereby the undesired cis α, α enantiomer is selectively crystallized from solution using (−)−2,3:4,6-di-O-isopropylidine-2-keto-L-gulonic acid hydrate (DAG), thereby providing mother liquors containing an enhanced proportion of the desired cis β, β enantiomer.

DESCRIPTION OF THE INVENTION

The present invention provides a method of resolving cis α, α/β, β azetidinone represented by the following two enantiomers:

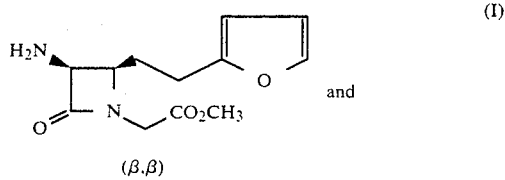

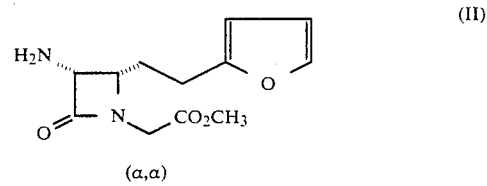

to yield optically pure isomers, each free of the other, which comprises mixing at least 0.5 molar equivalent of (−)−2,3:4,6-di-O-isopropylidine-2-keto-L-gulonic acid hydrate (DAG) with a polar organic solution of (I) and (II) to provide an insoluble salt of (II), which is removed, thereby providing a solution enhanced in proportion of (I).

Thus, the present invention provides a method whereby commercially-available (−)−2,3:4,6-di-O-isopropylidine-2-keto-L-gulonic acid hydrate (DAG) (Hoffman-LaRoche Inc., Nutley, NJ) is utilized to selectively crystallize, in high yield and purity, the salt of compound (II) above, which can then be removed mechanically, thereby affording a solution greatly enhanced in proportion of isomer (I) above. According to this method, a portion of a racemic mixture of (I) and (II) is dissolved in a polar organic solvent such as methanol, ethanol, 2-propanol, tetrahydrofuran, dimethoxyethane or acetonitrile in a concentration of about 1 to 2 molar and the solution is mixed with a 1-2 molar solution of 0.5 to 1.0 equivalents of DAG in the same solvent. Isopropanol is the preferred solvent, and additionally, up to 50% of a non-polar diluent such as heptane may be added to enhance the crystallization. Preferably the resulting solution is then seeded with crystals of the DAG salt of (II). However, selective crystallization of the amine salt will occur without seeding. The resulting mixture is allowed to crystallize and the resulting DAG salt of (II) is then collected. Typically, the salt of (II) is obtained in high yield with very high enantiomeric purity thereby leaving a mother liquor solution greatly enhanced in concentration of (I). The resolved free amine (I) can then be recovered by conventional methods from the remaining solution.

According to one method a concentrated solution of L(+)-tartaric acid in a mixture of water and isopropanol can be mixed with the solution of I and the L(+) tartrate salt of (I) crystallizes in high yield and high enantiomeric purity. This method is claimed in U.S. application Ser. No. 07/386,664.

The diastereomeric salt of II formed in the above process can be separated from the resolution mixture and the free amino azetidinone recovered from the salt forms by conventional methods. For example, the separated salt can be treated in an aqueous medium with a base to form the free amine which can be extracted from the aqueous phase with a water immiscible solvent such as ethyl acetate or methylene chloride. The process provides a high degree of separation of the two enantiomeric azetidinones as reflected by the observed enantiomeric excess (ee) of the product.

Alternatively, the solution of (I) can be used as is for subsequent processing. Thus, the present invention is useful in that the desired $\beta, \beta$ isomer (I) is provided in high enantiomeric purity, a step necessary for the total synthesis of 1-carbon(dethia)cephems.

The invention is further described by the following examples which are not to be construed as limiting any aspect of the invention.

EXAMPLE 1

DAG (2,3,4,6-di-0-isopropylidene-2-keto-L-gulonic acid hydrate) (0.5846 gm, 0.002 mole) was weighed into a 20 ml vial, and a solution of racemic cis 3-amino-4-[2-(2-furyl)eth-1-yl]-1-methoxycarbonyl-methylazetidin-2-one (0.50 gm, 0.002 mole) in ethanol (2 ml) was added and washed in with an additional 2 ml ethanol. A clear yellow solution was obtained on warming to 40° C. On cooling a voluminous precipitate formed. After standing overnight in the refrigerator, the crystals were isolated by vacuum filtration and washed with a little ice cold ethanol and dried under vacuum (0.1879 gm, 0.0003568 moles, 17.84% yield (where 50% is the maximum yield expected). The chiral assay showed 0.2% $\beta$, $\beta$ isomer and 99.8% $\alpha$, $\alpha$ isomer for an enantomeric excess of (−) 99.6%.

In a confirming, larger scale experiment, 8.63 gm (0.0342 mole) of the racemic cis amino azetidinone was dissolved in ethanol (20 ml) and added dropwise to a solution of DAG (10 gm, 0.034 mole) in ethanol (40 ml). No crystals formed on stirring overnight at room temperature. The mixture was seeded with crystals from the first experiment and refrigerated at 0° C. for 3 hours. The mixture solidified. The crystals were filtered off and washed with small amounts of ice cold ethanol and dried (6.27 gm, 0.0119 moles, 34.8% (maximum 50%), chiral assay: 0.7% $\beta$, $\beta$ 99.3% $\alpha$, $\alpha$; enantiomeric excess (−) 98.6%).

EXAMPLE 2

A 38.58 g (0.132 mol) sample of DAG was dissolved in 150 ml of isopropanol by warming to about 40° C. A solution of 0.2 moles of cis 3-amino-4-[2-(2-furyl)eth-1-yl]-1-methoxycarbonylmethyl-azetidin-2-one in 200 ml of isopropanol was added to the solution of DAG and the solution seeded with authentic crystals of the DAG salt of cis-$\alpha$, $\alpha$-3-amino-4-[2-(2-furyl)eth-1-yl]-1-methoxycarbonylmethyl-azetidin-2-one. The solution was then heated to 45° C. and an additional 50 ml of isopropanol added. The solution was then allowed to cool slowly over a 2 h period to 30° C. and then to room temperature overnight. The solution was then chilled in ice to 10° C. for 1 h and filtered. The resulting solid was washed sequentially with 100 ml of cold isopropanol, 100 ml of (1:1) isopropanol/hexane, and then with 100 ml of hexane to provide 45.69 g of a fine white solid. (86.8% yield, chiral assay (−) 100%, potency assay 102% of the $\alpha\alpha$ isomer)

The resulting mother liquors were then evaporated in vacuo, redissolved in 200 ml of $CH_2Cl_2$ and layered with 20 ml of water. The aqueous layer was adjusted to pH 7 with saturated sodium carbonate solution. The resulting organic phase was then washed sequentially with 30 ml of water containing about 1 ml sodium carbonate solution. The $CH_2Cl_2$ phase was then evaporated in vacuo to provide 31.1 g of an oil (81.8% enantiomeric excess); potency assay = 84.1% of the $\beta\beta$ isomer.

EXAMPLE 3

Isolation of $\beta, \beta$ Isomer as Tartrate Salt

Racemic cis-3-amino-4-[2(furyl)eth-1-yl]-1-methoxycarbonylmethylazetidin-2-one oxalate salt (69.7 gm, 0.2 moles) was treated with 40% aqueous potassium carbonate solution (~69 ml) in a mixture of dichloromethane (300 ml) and water (50 ml) to give a final pH ~7.4 The lower dichloromethane layer containing the free racemic cis-3-amino-4[2(2-furyl)eth-1-yl]-1-methoxy-carbonylmethylazetidin-2-one was separated, washed with water and the solvent removed under vacuum to yield an oil (55.81 gm), which was redissolved in warm (45° C.) isopropanol (70 ml). This solution was added to a warm (45° C.) solution of DAG ((−)2,3,4,6-di-O-isopropylidene-2-keto-L-gulonic acid hydrate)(32.5 gm, 0.11 mole) in isopropanol (100 ml), and washed in with warm isopropanol (2×50 ml). The solution was diluted with warm (45° C.) heptane (180 ml) and seeded. After ~5 minutes, crystallization was heavy and the mixture was cooled slowly (~4 hours) to 5° C. and filtered. The filter cake of the DAG salt of the cis $\alpha, \alpha$ 3-amino-4-[2-(2-furyl)eth-1-yl]-1-methoxycarbonylmethylazetidin-2-one (II) was washed with a cold mixture of isopropanol (180 ml) and heptane (80 ml) in small portions to remove the mother liquor which is enriched in the $\beta, \delta$ isomer (I). The DAG salt was dried under vacuum to yield 46.22 gm, (87%): potency assay 105%, chiral assay 0.7$\beta$, $\beta$, 99.3% $\alpha$, $\alpha$, for an enantiomeric excess of (−) 98.6%. The enriched mother liquor was concentrated to a weight of 142 gm and added to a warm (45° C.) solution of L (+) tartaric acid in water (13 ml) +isopropanol (50 ml). The solution was washed in with warm isopropanol (50 ml), and additional warm isopropanol added (~40 ml) until the solution just became cloudy at 44° C. The solution was seeded and warmed to 45° C. to dissolve cloudiness. When crystallization was well established in ~20 min, an additional ~10 ml isopropanol was added dropwise and the mixture cooled to 5° C. over ~3.5 hours. The L(+) tartrate salt of cis $\beta$, $\beta$-3-amino-4-[2-(2-furyl)eth-1-yl]-1-methoxy-carbonylmethylzaetidin-2-one (I) was washed with cold 4% water in isopropanol (100 ml), then cold isopropanol (100 ml) and heptane (50 ml) and dried under vacuum to yield 36.24 gm (89%); potency assay 96.3%; chiral assay 96.2% $\beta$, $\beta$, 3.8% $\alpha$, $\alpha$, for an enantiomeric excess of 92.4%.

EXAMPLE 4

DAG Resolution (Pilot Plant Scale)

A 300 gal reactor was charged with water (77 L) and methylene chloride (288 L), and the oxalate salt of racemic cis 3-amino-4-[2-(2-furyl)eth-1-yl]-1-methoxycarbonylmethylazetidin-2-one (64.3 Kg, potency 92.2%, ∴ 59.3 BKg, 173 moles) added to form a thick slurry, at 20-25° C., pH 1.9. Triethylamine (~39 Kg, 385 moles) was added to dissolve the solids at a final pH of 6.5. The two liquid layers were allowed to separate and the lower methylene chloride layer containing the racemic amino azetidinone free base was removed to a 200 gal reactor. The residual water layer was extracted with an additional 60 L methylene chloride which was combined with the original extract. The combined methylene chloride extracts were distilled under vaccum to remove the solvent, with a maximum reactor temperature of 34° C. The liquid residue was dissolved in isopropanol (46 L) and vacuum distilled again to a temperature of 30° C. at 1.9 psia. The racemic cis free amine residue was again dissolved in isopropanol (76 L), and heated to 42-45° C.

A 100 gal reactor was charged with isopropanol (152 L) and DAG (36.6 Kg, 125 moles), and heated to 42-45° C. This solution was added to the solution of racemic cis free amine and washed in with additional isopropanol (26 L), maintaining the reactor temperature at 42-45° C. Heptane (170 L) was then added and the solution was seeded. Crystallization began in ~2 min. After 30 min. stirring, cooling of the reactor was begun, and in 2.25 hours Temp was 20° C. After 2 hours more stirring, the DAG salt of the cis α, α amino azetidinone isomer was filtered off using a 36' diameter single plate filter. The filter cake was washed with a mixture of isopropanol (80 L) and heptane (53 L) in two portions, and then with heptane (57 L), and dried in an air dryer. The DAG salt weighed 35.4 Kg (77.7%, chiral assay: β, β 0.8%, α, α 99.2%; enantiomeric excess 98.4%).

The mother liquor containing almost all the desired cis β, β-amino azetidinone isomer was distilled under vacuum to remove the solvents. Final temperature 22° C. at 0.5 psia. The oily amino azetidinone+excess DAG residue was dissolved in methylene chloride (192 L) and water (43 L) and the pH adjusted from 4.2 to 7.6 by addition of triethylamine (5.6 Kg). The layers were separated and the lower organic layer containing the free cis amino azetidinone (enriched in the β, β isomer) removed to a 300 gal reactor. The upper water layer containing the DAG was washed with an additional 50 L portion of methylene chloride which was combined with the first extract. The combined methylene chloride extracts were washed with an additional 15 L portion of water, and the lower layer removed to a 200 gal reactor. The enantiomeric excess in this solution was calculated to be 77.9%.

EXAMPLE 5

According to the general procedure below and the subsequent table, the optimum parameters of the process is illustrated.

To a 2-liter, 3-necked round bottom flask equipped with a mechanical stirrer and thermometer are added DAG (0.55 eq. 0.275 mole, 80.38 g) and 275 ml isopropanol. The mixture is heated to 45° C. to dissolve the material. In a separate vessel racemic cis 3-amino-4-[2-(2-furyl)eth-1-yl]-1-methoxycarbonylmethyl-azetidinone (I & II), (0.50 mole, 128.0 g prepared from 0.5 mole, 173.23 g, 98.8% pure oxalate salt (of the mixture of I and II) using methylene chloride and aqueous triethylamine) and 150 ml of isopropanol are combined and the solution is heated to 40° C. At 40-45° C. the solution is added to the DAG/isopropanol solution. The solution of the free base is rinsed in with 250 ml isopropanol. The resulting solution is seeded at 45° with the DAG salt of II and at 38-45° C. 450 ml heptane are added over 2 minutes. The DAG salt crystallizes rapidly. The slurry is held at 45° C. for 10 minutes and then is allowed to cool to 30° C. over 2 hours. The slurry then is cooled to 5° C. over 1.5 hours and held at that temperature for 1 hour. The DAG salt is filtered, rinsed out of the flask with 2×25 ml of 3:2 isopropanol/heptane cooled to 5° C. The filtercake is washed with 2×150 ml of 3:2 isopropanol/heptane cooled to 5° C. and with 1×150 mol heptane at room temperature. The filtercake is dried at 30° C./vac. Yield 114.14 g, 86.8%, of the DAG salt of II. ee= −96.8%, MP=119-121° C. MP=124.0-4.5° C. for ee= −100.0%.

The DAG filtrate is concentrated at 40° C./vac to an oil (92.63 g) and the oil dissolved in 500 ml methylene chloride and 40 ml water in a 1 liter, 3-necked round bottom flask (pH 4.6). Approx. 14 ml sat'd sodium carbonate solution is added to give pH 7.1 and the bottom layer is separated. The remaining aqueous layer is extracted with 15 ml methylene chloride the bottom organic layer is separated. The two organic layers are combined and extracted with 35 ml water. The bottom organic layer containing the desired free base isomer is separated. Organic layer weight=730.0 g (density 1.27 g/ml, calc. 72.8 g net free base without solvent ee 84.4%, potency 80.5%.

The following table lists the results obtained in a number of runs of the resolution process. In examples 24 to 30, an isopropanol (IPA)/methylene chloride azeotrope was utilized to remove water from the solution

| | | | | | Examples 6-38 | | |
|---|---|---|---|---|---|---|---|
| Ex. | % Yield DAG Salt | % ee DAG Salt | % ee Filtrate | Eg DAG | Solvent(s) | L/Mol. | Comments |
| 6 | 84.8 | −99.6 | 85.0 | 0.66 | IPA | 2.0 | |
| 7 | 86.1 | −100.0 | 86.6 | 0.55 | IPA | 2.0 | Slow filtering |
| 8 | 85.2 | −100.0 | 86.0 | 0.66 | IPA | 2.0 | FIltered at −10° |
| 9 | 85.3 | −99.4 | 84.2 | 0.66 | IPA | 3.0 | Filtered at −10° |
| 10 | 82.6 | −93.4 | 76.8 | 0.66 | IPA | 3.0 | Dist. IPA to remove H₂O, filtered −10° |
| 11 | 83.5 | −98.0 | 79.8 | 0.51 | IPA/Hept 1:1 | 2.0 | |
| 12 | 102.1 | −51.2 | 80.6 | 0.51 | IPA/Hept 1:1 | 2.0 | Cake not washed |
| 13 | 85.2 | −100.0 | 84.0 | 0.51 | IPA/Hept 3:2 | 2.0 | |
| 14 | 93.0 | −82.0 | 84.0 | 0.51 | IPA/Hept 3:2 | 2.0 | Cake not washed |
| 15 | 88.3 | −99.6 | 85.4 | 0.87 | IPA/Hept 7:2 | 2.3 | |
| 16 | 83.1 | −99.6 | 80.4 | 0.66 | i-BuOH | 2.0 | |
| 17 | 83.6 | −100.0 | 82.6 | 0.55 | n-PrOH | 2.0 | |
| 18 | 85.2 | −99.6 | 84.6 | 0.66 | IPA | 2.0 | |

-continued

Examples 6-38

| Ex. | % Yield DAG Salt | % ee DAG Salt | % ee Filtrate | Eg DAG | Solvent(s) | L/Mol. | Comments |
|---|---|---|---|---|---|---|---|
| 19 | 86.8 | −100.0 | 81.8 | 0.66 | IPA | 2.0 | |
| 20 | 87.2 | −99.4 | 86.2 | 0.66 | IPA/Hept 7:2 | 2.3 | |
| 21 | 86.8 | −96.8 | 84.4 | 0.55 | IPA/Hept 3:2 | 2.3 | Solvent Exchange & H$_2$O Azeotrope (Using CH$_2$Cl$_2$/isopropanol azeotrope) |
| 22 | 76.9 | −98.2 | 77.8 | 0.55 | IPA | 1.5 | CH$_2$Cl$_2$ exchange to IPA |
| 23 | 88.9 | −97.6 | 87.8 | 0.55 | IPA/Hept 3:2 | 2.6 | CH$_2$Cl$_2$ exchange to IPA/Heptane |
| 24 | 84.8 | −99.2 | 85.4 | 0.55 | IPA | 3.0 | Dist. isopropanol (IPA) to remove H$_2$O f. DAG, incl. base |
| 25 | 88.1 | −91.2 | 79.6 | 0.51 | IPA/Hept 3:2 | 2.3 | Dist. IPA to remove H$_2$O f. DAG, incl. base |
| 26 | 86.7 | −98.2 | 84.4 | 0.55 | IPA/Hept 3:2 | 3.0 | Dist. IPA to remove H$_2$O f. DAG, incl. base |
| 27 | 88.0 | −100.0 | 87.6 | 0.55 | IPA/Hept 3:2 | 3.0 | Dist. IPA to remove H$_2$O from DAG only |
| 28 | 86.3 | −98.6 | 84.2 | 0.55 | IPA/Hept 3:2 | 3.0 | Dist. IPA to remove H$_2$O from DAG only |
| 29 | 99.1 | −86.0 | 87.2 | 0.74 | IPA/Hept 3:2 | 3.0 | Dist. IPA to remove H$_2$O from DAG only |
| 30 | 83.7 | −97.2 | 83.0 | 0.74 | IPA/Hept 3:1 | 3.0 | Dist. IPA to remove H$_2$O from DAG only |
| | | | | | | | Isolation Correct Isomer as Salt, Solvent, % Yld, % ee c = calc |
| 31 | 86.9 | −99.4 | 83.0 | 0.67 | IPA/Hept 3:1 | 2.3 | Tartrate, ACN/H$_2$O, 76.9%, 97.6% ee |
| 32 | 88.1 | −99.6 | 85.0 | 0.74 | IPA/Hept 7:2 | 2.3 | Tartrate, ACN/H$_2$O, 77.7%, 99.2% ee |
| 33 | 88.9 | −99.8 | 86.8 | 0.97 | IPA/Hept 7:2 | 2.3 | Tartrate, ACN/H$_2$O, 74.8%, 98.8% ee |
| 34 | 86.8 | −98.8 | c 75.8 | 0.55 | IPA/Hept 3:2 | 2.3 | Tartrate, IPA/H$_2$O, 88.9%, 92.8% ee |
| 35 | 85.6 | −99.6 | c 74.4 | 0.55 | IPA/Hept 3:2 | 2.3 | Tartrate, IPA/H$_2$O, 88.4%, 92.8% ee |
| 36 | 87.8 | −97.4 | c 76.2 | 0.55 | IPA/Hept 3:2 | 2.3 | Tartrate, IPA/H$_2$O, 88.1%, 94.4% ee |
| 37 | 87.1 | −98.6 | c 76.2 | 0.55 | IPA/Hept 3:2 | 2.3 | Tartrate, IPA/H$_2$O, 89.4%, 92.4% ee |
| 38 | 85.7 | −98.0 | c 73.6 | 0.52 | IPA/Hpet 3:2 | 2.3 | Oxalate, IPA/MeOH, 89.6%, 78.0% ee |

We claim:

1. The (−)-2,3:4,6-di-O-isopropylidene-2-keto-L-gulonic acid hydrate salt of cis αα-3-amino-4-[2-(2-furyl)eth-1-yl]-1-methoxycarbonylmethylazetidin-2-one.

* * * * *